US009870904B2

(12) United States Patent
Covey et al.

(10) Patent No.: US 9,870,904 B2
(45) Date of Patent: Jan. 16, 2018

(54) ION SOURCE FOR MASS SPECTROMETRY (71) Applicant: DH Technologies Development PTE Ltd., Singapore (SG)

(72) Inventors: Thomas R Covey, Richmond Hill (CA); Peter Kovarik, Markham (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 15/104,638

(22) PCT Filed: Oct. 31, 2014

(86) PCT No.: PCT/IB2014/002461
§ 371 (c)(1),
(2) Date: Jun. 15, 2016

(87) PCT Pub. No.: WO2015/092501
PCT Pub. Date: Jun. 25, 2015

(65) Prior Publication Data
US 2017/0032949 A1    Feb. 2, 2017

Related U.S. Application Data

(60) Provisional application No. 61/919,125, filed on Dec. 20, 2013.

(51) Int. Cl.
*H01J 49/00* (2006.01)
*H01J 49/04* (2006.01)
(Continued)

(52) U.S. Cl.
CPC .......... *H01J 49/045* (2013.01); *G01N 30/724* (2013.01); *H01J 49/044* (2013.01);
(Continued)

(58) Field of Classification Search
CPC .... H01J 49/045; H01J 49/0404; H01J 49/167; H01J 49/044; G01N 30/724; G01N 30/7246; G01N 30/7273
(Continued)

(56) References Cited

U.S. PATENT DOCUMENTS 3,418,513 A    12/1968 Elliott
4,112,297 A    9/1978 Miyagi et al.
(Continued)

FOREIGN PATENT DOCUMENTS

CA    WO 2012028940 A2 *    3/2012 ............. H01J 49/04
WO    2009-124298 A2    10/2009

OTHER PUBLICATIONS

International Search Report and Written Opinion for PCT/IB2014/002461 dated Feb. 27, 2015.

*Primary Examiner* — Michael Maskell (57) ABSTRACT

Systems and methods for delivering a sample to a mass spectrometer are provided. In one aspect, the systems and methods can provide efficient cooling of an ion source probe to prevent overheating and the resulting degradation in ion sampling. In some aspects, such cooling can result in improved consistency and/or efficiency of ion formation. Moreover, ion source cooling in accordance with various aspects of the present teachings can allow for the use of higher temperatures in the ionization chamber (thereby improving desolvation) and/or can enable the use of lower flow rate sample sources than with conventional techniques.

18 Claims, 5 Drawing Sheets

(51) Int. Cl.
  *H01J 49/16* (2006.01)
  *G01N 30/72* (2006.01)
(52) U.S. Cl.
  CPC ........ *H01J 49/0404* (2013.01); *H01J 49/167* (2013.01); *G01N 30/7246* (2013.01); *G01N 30/7273* (2013.01)
(58) Field of Classification Search
  USPC .................................................. 250/288, 425
  See application file for complete search history.

(56) References Cited

U.S. PATENT DOCUMENTS

| | | | |
|---|---|---|---|
| 7,189,977 B2* | 3/2007 | Yamaguchi | H01J 49/165 250/288 |
| 9,552,971 B2* | 1/2017 | Kovarik | H01J 49/0431 |
| 2013/0213150 A1* | 8/2013 | Covey | H01J 49/0422 73/863.41 |

* cited by examiner

ION SOURCE FOR MASS SPECTROMETRY

RELATED APPLICATION

This application claims priority to U.S. provisional application No. 61/919,125, filed on Dec. 20, 2013, which is incorporated herein by reference in its entirety.

FIELD

The present teachings relate to methods, systems and apparatus for generating ions from a sample (e.g., containing an analyte of interest) for mass spectrometric analysis.

INTRODUCTION

Mass spectrometers allow detection, identification, and quantification of chemical entities in samples. Mass spectrometers detect the chemical entities as ions such that a conversion of the chemical entities to charged ions must occur during the sampling process. Liquid samples are conventionally converted into gas phase by employing atomizers, nebulizers, and/or electro sprayers, which can produce a plume of liquid sample droplets (e.g., a plurality of micro droplets entrained in a carrier gas directed toward a sampling orifice of a mass spectrometer). Often a desolvation step is utilized in the sampling process to dry the sample droplets to enhance the release of the ionic species. For example, as described in U.S. Pat. No. 5,412,208, desolvation techniques often utilize a flow of heated gas to intersect the plume or spray of droplets generated by a sample probe within the sampling chamber. The flows mix turbulently, with the heated gas helping to move the droplets toward the orifice of the mass spectrometer and evaporate the droplets to generate ions for downstream mass spectrometric analysis.

Conventional desolvation techniques utilizing elevated temperatures, however, can pose challenges that adversely affect the performance of the mass spectrometer, especially during extended sampling runs and/or in combination with low flow rate sample sources (e.g., liquid chromatography (LC) based separation processes).

Accordingly, there is a need for enhanced systems, methods, and devices for preparing and delivering a sample to a mass spectrometer.

SUMMARY

Though the use of elevated temperatures within the ionization chamber may be necessary to improve desolvation of the sample stream, and thus improve sampling efficiency, conventional desolvation techniques can cause adverse thermal effects on the ion source probe (e.g., a stainless steel capillary tube), which extends into the heated ionization chamber. As the ion source probe heats up, the flow of sample liquid within the probe can be vaporized, thereby causing instability in the generation of the sample plume. By way of example, as the vaporizing liquid rapidly expands within the probe, some sample liquid downstream of this vapor "plug" may be ejected more forcefully from the probe, thereby increasing the flow rate of liquid sample ejected from the probe, the size of the plume discharged by the probe, and/or the velocity of the fluid droplets within the plume. Moreover, as the vapor plug itself is discharged from the probe into the ionization chamber, the transmission of ions into the mass spectrometer can be interrupted as the probe is temporarily dry.

Apparatus, systems, and methods in accordance with the applicants' present teachings address the overheating of the ion source probe and the resulting degradation of ion sampling (and ultimately diminished mass spectrometer performance), by providing efficient cooling of the ion source probe. In various aspects, such cooling can result in improved consistency and/or efficiency of ion formation. Moreover, in some aspects, apparatus, systems, and methods in accordance with the present teachings can enable the ionization chamber to be heated to higher temperatures than in conventional techniques to allow for improved desolvation of the sample within the ionization chamber. Ideally, the present teachings enable the complete desolvation/ionization of the liquid sample directly in front of the orifice leading to a downstream mass spectrometer. Additionally, as low flow rate liquid samples may be particularly affected by overheating of the ion probe, the present teachings may enable the use of lower flow rate sample sources relative to conventional techniques.

In one aspect, a mass spectrometry system is disclosed, which includes a mass spectrometer having a sampling orifice for receiving ions from an ion source having a sample conduit (e.g., ESI electrode probe) for discharging a liquid sample into a chamber in fluid communication with the sampling orifice. The conduit extends from a proximal, inlet end configured to receive a liquid sample from a sample source and terminates in a distal, outlet end extending into the chamber. A sheath surrounds the sample conduit so as to define a channel between an inner wall of the sheath and the conduit, the channel being configured to provide a nebulizer gas flow (e.g., $N_2$, air, a noble gas, etc.) at the outlet end of the sample conduit for generating a sample plume comprising a plurality of droplets of the discharged sample and the nebulizer gas directed toward (e.g., in the vicinity of) the sampling orifice. The ion source also includes a cooling conduit having an outlet for delivering a cooling fluid to the channel so as to cool and/or prevent overheating of the sample conduit. For example, the outlet of the cooling conduit can be configured to deliver the cooling fluid onto a surface of the sample conduit within the sheath for removing heat therefrom, e.g., by way of evaporation of the cooling liquid upon contact with said sample conduit.

The cooling conduit can have a variety of configurations, but is generally configured to deliver the cooling fluid into thermal contact (e.g., direct physical contact or otherwise) with the sample conduit. By way of example, the outlet of the cooling conduit can comprise a nozzle for generating a spray of the cooling fluid within said channel (e.g., onto the surface of the sample conduit). In some aspects, the cooling conduit is at least partially disposed within the channel. In various aspects, the outlet of the cooling conduit can be configured to move axially within the channel between a first, proximal position and a second, distal position. Such movement of the outlet end of the cooling conduit can be effective to modify a rate of cooling of the sample conduit.

In accordance with various aspects of the present teachings, the rate of cooling of the sample conduit can alternatively or additionally be adjusted by selecting at least one of a fluid flow rate of cooling fluid, a position of the outlet of the cooling conduit, and a composition of the cooling fluid so as to control a temperature of the sample conduit. By way of example, one or more of the fluid flow rate of the cooling fluid, the position of the outlet of the cooling conduit, and the composition of the cooling fluid can be selected so as to maintain the sample conduit at a temperature below about 60° C. substantially along its entire length. In some aspects, for example, the ion source can include a pump for delivering the cooling fluid and for controlling a rate of cooling fluid flow through the cooling conduit. In some aspects, the ion source can include a cooling fluid source (e.g., a reservoir of cooling fluid) fluidly coupled to the cooling conduit.

The cooling fluid can be any fluid capable of cooling the sample conduit in accordance with the present teachings. By way of example, the cooling fluid can be selected such that substantially all of the cooling fluid discharged into the channel changes its phase following contact with the conduit (e.g., prior to ejection into the ionization chamber). In some aspects, the cooling fluid comprises one or more of water and methanol, by way of non-limiting example. Additionally or alternatively, the cooling fluid can be substantially chemically inert with the liquid sample. In some aspects, where the sample source comprises a liquid chromatography (LC) column, the cooling fluid can comprise the solvent used to elute the liquid sample from the LC column, for example.

The ion source can generate a sample plume and/or ionize the liquid sample utilizing any mechanism known in the art and modified in accordance with the present teachings. By way of example, the sample conduit can comprise a capillary tube that can be energized to ionize the liquid sample as it is discharged in the chamber. In some aspects, the sample conduit can comprise an electrospray ionization (ESI) electrode.

In various aspects, the ion source or mass spectrometer system can include at least one heater for heating the chamber to promote desolvation of the plurality of fluid droplets within the sample plume. For example, the heater can be configured to heat the chamber to a temperature in a range of about 100° C. to about 800° C. In some aspects, the at least one heater can be configured to generate a stream of heated gas substantially directed to a region within said chamber between the outlet end of the sample conduit and the sampling orifice. Alternatively or additionally, the at least one heater can comprise heater coils.

In some aspects, the liquid sample can have a fluid flow rate through the sample conduit in a range of between about 1 µL/min to about 10 mL/min. For example, the fluid flow rate through said sample conduit can be less than about 20 µL/min (e.g., about 10 µL/min).

In another aspect, a method for directing ions to a mass spectrometer is disclosed, which comprises receiving a liquid sample from a sample source at an inlet end of a sample conduit extending through a channel defined by a sheath surrounding the sample conduit, providing a nebulizer gas flow within the channel, and discharging the liquid sample and the nebulizer gas flow into a chamber in fluid communication with a mass spectrometer via a sampling orifice, the liquid sample and the nebulizer gas flow forming a plume comprising a plurality of liquid sample droplets. The method can also include heating the chamber so as to promote desolvation of the plurality of droplets within the plume and delivering a cooling fluid into the channel so as to cool the sample conduit and/or prevent the sample conduit from overheating.

In some aspects, delivering the cooling fluid into the channel can comprise delivering (e.g., discharging, spraying) the cooling fluid onto a surface of the sample conduit within the sheath so as to remove heat from the sample conduit. In various aspects, the cooling liquid can remove heat from the sample conduit via evaporation of the cooling liquid upon contact with the sample conduit.

Additionally, in some aspects, the method can include adjusting a rate of cooling of the sample conduit. By way of example, adjusting the rate of cooling can comprise axially moving an outlet of a cooling conduit for delivering the cooling fluid between a first, proximal position and a second, distal position within the channel. Alternatively or additionally, adjusting a flow rate of cooling fluid delivered into the channel and/or adjusting the composition of the cooling fluid can be used to adjust the rate of cooling. In some aspects, one or more of the flow rate of cooling fluid, the position of the outlet of the cooling conduit, and the composition of the cooling fluid can be adjusted such that substantially all of the cooling fluid discharged into the channel changes phase prior to discharge from the channel into the chamber.

In another aspect, an ion source or mass spectrometry system incorporating the same is disclosed, the ion source comprising a chamber configured to be in fluid communication with a mass spectrometer system via a sampling orifice, a sample conduit for discharging a liquid sample into the chamber, the conduit extending from a proximal, inlet end configured to receive a liquid sample from a sample source and terminating in a distal, outlet end extending into the chamber. A sheath surrounds the sample conduit for providing a nebulizer gas flow at the outlet end of the sample conduit. A fluid flow channel containing a cooling fluid therein can be disposed in thermal communication with the sample conduit so as to maintain the sample conduit at a temperature below about 60° C. substantially along its entire length.

The fluid flow channel can have a variety of configurations, but generally contains one or more of a liquid or gas (e.g., a chilled fluid). In various aspects, for example, the sheath can define the fluid flow channel. In some aspects, the fluid flow channel extends through the sheath and can be in direct contact with walls of the sample conduit to remove heat therefrom.

Further understanding of the invention can be obtained by reference to the following detailed description in conjunction with the associated drawings, which are described briefly below.

BRIEF DESCRIPTION OF THE DRAWINGS

A skilled person in the art will understand that the drawings, described below, are for illustration purposes only. The drawings are not intended to limit the scope of the applicants' teachings in any way.

DETAILED DESCRIPTION

Those skilled in the art will understand that the methods, systems, and apparatus described herein are non-limiting exemplary embodiments and that the scope of the applicants' disclosure is defined solely by the claims. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art. The features illustrated or described in connection with one exemplary embodiment may be combined with the features of other embodiments. Such modifications and variations are intended to be included within the scope of the applicants' disclosure.

Apparatus, systems, and methods in accordance with the applicants' present teachings can provide efficient cooling of an ion source probe to prevent overheating and the resulting degradation in ion sampling. In various aspects, such cooling can result in improved consistency and/or efficiency of ion formation. Moreover, ion source cooling in accordance with various aspects of the present teachings can allow for the use of higher temperatures in the ionization chamber (thereby improving desolvation) and/or can enable the use of lower flow rate sample sources than with conventional techniques.

Figure 1:
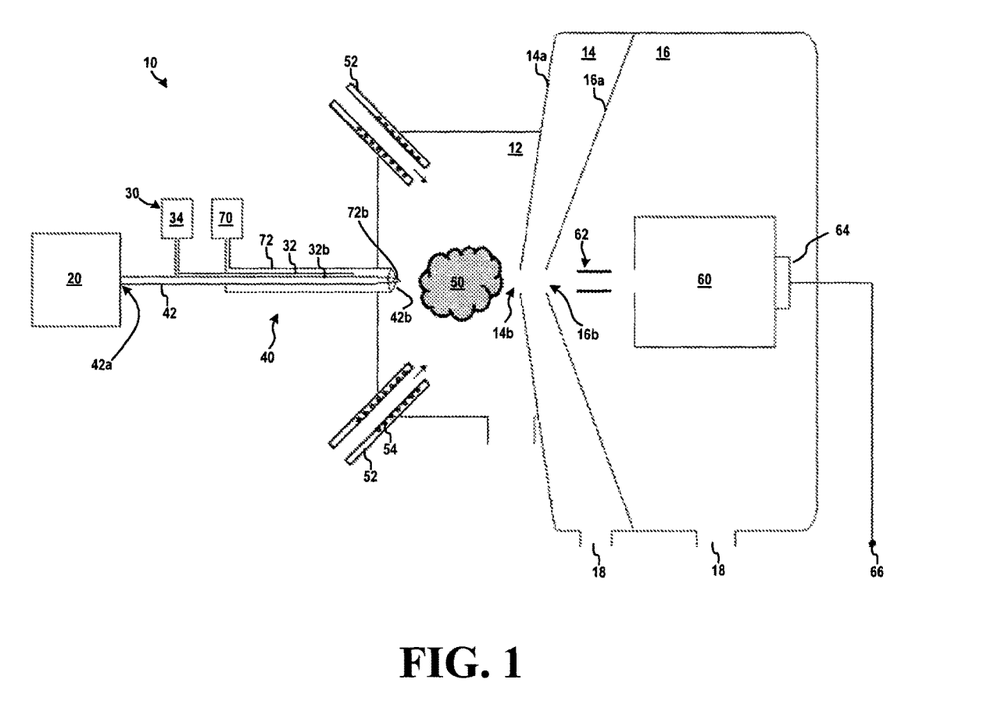
FIG. 1, in schematic diagram, illustrates an exemplary embodiment of a system for delivering a sample to a mass spectrometer according to various aspects of the applicants' teachings.

FIG. 1 schematically depicts an exemplary embodiment of a mass spectrometer system 10 in accordance with various aspects of the applicants' teachings for generating sample ions from a liquid sample and delivering the sample ions to a sampling orifice of a mass spectrometer. As shown in FIG. 1, the mass spectrometer system 10 generally includes a liquid sample source 20, an ion source 40 for discharging the liquid sample into a heated ionization chamber 12 so as to generate ions from the liquid sample, and a mass analyzer 60. As will be discussed in detail below, the exemplary ion source 40 also includes a cooling mechanism for removing heat from a sample conduit that receives the liquid sample from the sample source 20 and discharges the liquid sample into a heated ionization chamber 12.

As will be appreciated by a person skilled in the art, the system 10 can be fluidly coupled to and receive a liquid sample from a variety of liquid sample sources. By way of non-limiting example, the sample source 20 can comprise a reservoir of the sample to be analyzed or an input port through which the sample can be injected (e.g., manually or via an auto-sampler). Alternatively, also by way of non-limiting example, the liquid sample to be analyzed can be in the form of an eluent from a liquid chromatography column.

As shown in FIG. 1, the mass spectrometry system 10 can include one or more vacuum chambers 14, 16 within which the ions generated by the ion source 40 can be received and/or processed. By way of example, in the depicted embodiment, the ionization chamber 12 can be separated from a gas curtain chamber 14 by a plate 14a having a curtain plate aperture 14b. As shown, a vacuum chamber 16, which houses the mass analyzer 60, is separated from the curtain chamber 14 by a plate 16a having a vacuum chamber sampling orifice 16b. The ionization chamber 12 can be maintained at an atmospheric pressure, though in some embodiments, the ionization chamber 12 can be evacuated to a pressure lower than atmospheric pressure. The curtain chamber 14 and vacuum chamber 16 can be maintained at a selected pressure(s) (e.g., the same or different sub-atmospheric pressures, a pressure lower than the ionization chamber 12) by evacuation through one or more vacuum pump ports 18. Ions generated by the ion source 40 in the ionization chamber 12 can thus be drawn through orifices 14b, 16b positioned generally along the axis of the mass spectrometer system 10 and can be focused (e.g., via one or more ion lens 62) into the mass analyzer 60.

The mass analyzer 60 can have a variety of configurations but is generally configured to process (e.g., filter, sort, dissociate, detect, etc.) sample ions generated by the ion source 40. By way of non-limiting example, the mass analyzer 60 can be a triple quadrupole mass spectrometer, or any other mass analyzer known in the art and modified in accordance with the teachings herein. It will further be appreciated by a person skilled in the art in light of the present teachings, that a detector 64 at the end of the mass analyzer 60 can detect the ions which pass through the analyzer 60 and can, for example, supply a signal at terminal 66 indicative of the number of ions per second that are detected.

The ion source 40 can have a variety of configurations but generally comprises a sample conduit for receiving a liquid sample from the sample source 20 and for discharging the liquid sample into the ionization chamber 12. As shown in FIG. 1, the exemplary ion source 40 includes an ion probe 42 (e.g., a capillary tube) that is fluidly coupled to the sample source 20 for receiving the liquid sample at its inlet end 42a. The liquid sample is transmitted (e.g., pumped via an LC pump) through the ion probe 42 and discharged through its outlet port 42b, which at least partially extends into the ionization chamber 12.

In accordance with various aspects of the present teachings, the ion source 40 can additionally include a sheath, within which the ion probe 42 is at least partially disposed along its length. As shown in FIG. 1, for example, the sheath can comprise a nebulizer shaft 72 that surrounds the ion probe 42 and defines a channel between an inner wall of the nebulizer shaft 72 and an outer wall of the ion probe 42. A source 70 of pressurized gas (e.g. nitrogen, air, or a noble gas) can be coupled to the sheath 72 in order to supply a nebulizing gas flow which surrounds the outlet end 42b of the ion probe 42 and interacts with the fluid discharged therefrom to enhance the formation of the sample plume 50 and the ion release within the plume, e.g., via the interaction of the high speed nebulizing flow and the jet of liquid sample. The nebulizer gas can be supplied at a variety of flow rates, for example, in a range from about 0.1 L/min to about 20 L/min.

Thus, as will be appreciated by a person skilled in the art in light of the present teachings, the outlet end 42b can atomize, aerosolize, nebulize, or otherwise discharge (e.g., spray with a nozzle) the liquid sample into the ionization chamber 12 to form a sample plume 50 comprising the nebulizing gas flow and a plurality of micro-droplets of the liquid sample generally directed toward (e.g., in the vicinity of) the curtain plate aperture 14b and sampling orifice 16b. As is known in the art, analyte molecules contained within the micro-droplets can be ionized (i.e., charged) by the ion source 40, for example, as the sample plume 50 is generated. By way of non-limiting example, the outlet end 42b of the ion probe 42 can be made of a conductive material and electrically coupled to a pole of a voltage source (not shown), while the other pole of the voltage source can be grounded. The nebulizer output 72b (e.g., nozzle) can supply a high velocity nebulizing gas flow which nebulizes the fluid ejected from the outlet end 42b. Micro-droplets contained within the sample plume 50 can thus be charged by the voltage applied to the outlet end 42b of the ion probe 42 such that the liquid (e.g., solvent) within the droplets evaporates and the generated analyte ions are released and drawn toward and through the apertures 14b, 16b (e.g., 14a, 16a can be made electrically attractive to the ions/droplets). It will be appreciated that a number of different mechanisms known in the art and modified in accord with the teachings herein can be utilized in the ion source 40. By way of non-limiting example, the sample source 40 can be an electrospray ionization device, a nebulizer assisted electrospray device, chemical ionization device, nebulizer assisted atomization device, a thermospray ionization device, and a sonic spray ionization device.

As shown in FIG. 1, the exemplary mass spectrometer system 10 additionally includes one or more heaters 52 for heating the ionization chamber 12 to promote desolvation of the liquid (e.g., solvent) within the sample plume 50. By way of example, the heater(s) 52 can provide a flow of heated gas to the ionization chamber 12 (e.g., heated by heating elements 54), though the chamber can also be heated directly by one or more heating elements (e.g., coils) disposed therein. In some aspects, the heater(s) 52 can be effective to raise the temperature of the ionization chamber to a temperature in a range of from about 100° C. to about 800° C. The heater(s) 52 and the ion probe 42 can have a variety of configurations, but are generally positioned relative to one another and to the apertures 14b, 16b such that the heated gas flow directs the sample plume 50 to the proximity of the apertures 14b, 16b. In some embodiments, the ion probe 42 and the heater(s) 52 can be positioned relative to one another such that the heated gas stream intersects the sample plume 50 generated by the ion source 40 (e.g., at a region within the ionization chamber 12 between the outlet end 42b of the ion probe 42 and the aperture 14b).

Figure 2:
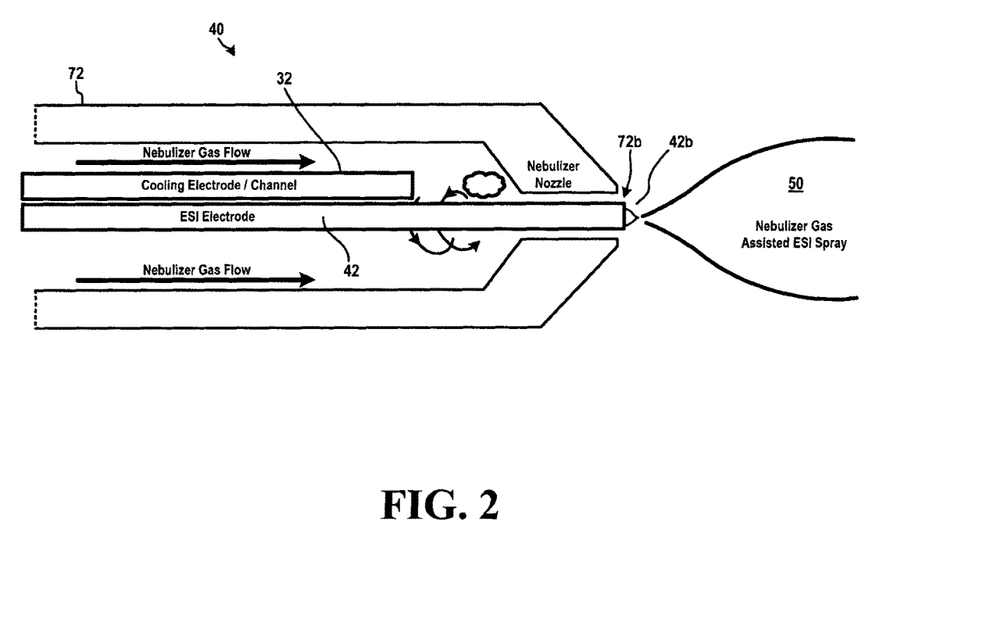
FIG. 2, in schematic diagram, illustrates in additional detail the exemplary embodiment of an ion probe cooling mechanism depicted in FIG. 1.

As indicated above, heating of the ionization chamber 12 via the one or more heaters 52 may, however, also cause thermal energy to be transferred to the ion probe 42 that extends into the heated ionization chamber. With reference now to FIGS. 1 and 2, one exemplary cooling mechanism 30 in accordance with various aspects of the present teachings is discussed in detail. As shown in these figures, the cooling mechanism 30 generally comprises a cooling conduit 32 that extends into the channel of the sheath 72 and through which a cooling fluid can flow. The cooling conduit 32, which can be fluidly coupled at its inlet end to a fluid reservoir 34 containing a supply of cooling fluid, terminates in a cooling fluid outlet 32b disposed within the sheath 72 such that cooling fluid can be discharged from the outlet 32b into the channel of the sheath 72. In some aspects, a pump (not shown) can be provided to deliver cooling fluid from the fluid reservoir (34) through the cooling conduit 32. Further, the outlet 32b can include a nozzle, for example, to aid in the distribution of the cooling fluid within the nebulizing gas flow channel and/or onto the surface of the ion probe 42. As cooling fluid is discharged from the outlet 32b, the nebulizer gas flow within the channel can also be effective to distribute the cooling fluid into contact with the heated source probe 42 to remove heat therefrom.

Cooling fluids can comprise any of a variety of liquids and/or gases that can be effective to remove heat from the cooling conduit 32 and/or probe 42 in accordance with the present teachings. By way of non-limiting example, the cooling fluid can be one of a chilled liquid and a chilled gas. Moreover, in some embodiments, preferable cooling liquids for use in accordance with the present teachings are chemically inert (e.g., non-reactive) with the molecules of the sample liquid. For example, the cooling fluid can be water, an alcohol (e.g., methanol), or a mixture thereof. In embodiments of the present teachings in which the sample source 20 is an LC column, for example, the solvent that is used to elute the liquid sample from the LC column can also be used as the cooling liquid to prevent any chemical interference from occurring with the analytes of interest within the liquid sample.

Though any number of fluids can be delivered by the cooling conduit 32 into the channel for removing heat from the ion probe 42, in a preferred embodiment, the cooling fluid comprises a liquid that can be discharged onto the surface of the conduit 42 such that substantially all (e.g., more than 90%) of the cooling liquid evaporates following contact with the ion probe 42 and prior to discharge into the ionization chamber 12 (e.g., via the flow of nebulizer gas). In such a manner, the cooling fluid can be effective to efficiently remove heat from the conduit 42 via evaporative cooling without diluting the liquid sample containing an analyte of interest that is discharged into the ionization chamber and/or without interfering with its ionization. Moreover, vapor resulting from the evaporation of the cooling liquid can exit the sheath 72 along with the nebulizer gas and assist in the nebulization process.

As will be appreciated by a person skilled in the art, because of the differences between the energy required to vaporize different liquids, the cooling liquid can be selected so as to optimize cooling of the ion probe 42, for example, while nonetheless ensuring that substantially all of the cooling fluid changes its phase prior to discharge into the ionization chamber. By way of example, because alcohol (e.g., methanol) is more readily vaporized than water (but ultimately provides a lower cooling potential per mole), the cooling liquid can comprise a mixture of water and alcohol in a ratio that is selected to achieve optimal cooling with minimal extraneous cooling liquid.

Similarly, the volumetric flow rate of the cooling liquid discharged into the channel from the cooling conduit 32 can also be adjusted to ensure optimal cooling of the ion source probe. By way of example, a pump (not shown) can be set and/or adjusted to provide the desired volumetric flow rate of the cooling fluid. Thus, if the temperature of the probe 42 increases during an extended sample run, the volumetric flow rate of coolant could be increased in order to extract more heat from the ion probe 42. Similarly, if the sample liquid within the probe 42 is stable and/or the probe 42 is not in danger of overheating, the flow rate of cooling liquid discharged from the conduit 32 can be decreased.

Further, as indicated by the arrows in FIG. 2, the position of the outlet 32b of the cooling conduit 32 within the channel can, in some embodiments, be adjusted to alter the axial position of the discharge of the cooling fluid relative to the outlet end of the ion probe 32. By way of non-limiting example, the cooling conduit 32 can be actuated to move from a proximal, retracted position to a distal, extended position if heat in the ion probe 42 is concentrated near the outlet 42b. Alternatively, the cooling conduit 32 can be retracted to a more distal position to provide for the extraction of heat from the ion probe 42 along a greater length. Likewise, if the cooling fluid requires additional time to vaporize, for example, the cooling conduit can be retracted to prevent cooling fluid from being discharged into the ionization chamber 12. As will be appreciated by a person skilled in the art in light of the present teachings, axial positioning of the cooling conduit 32 relative to the probe 42, can be implemented using a variety of techniques or actuators, whether mechanical, pneumatic, electric, or hydraulic (e.g., gears, cams, slides, screws, pistons, transducers, etc.), all by way of non-limiting example.

As will be appreciated by a person skilled in the art, a temperature of the ion probe 42 can be monitored (e.g., via a thermistor) to control modification of the cooling rate through modifying the volumetric flow rate of the cooling fluid, the composition of the cooling fluid, or the axial position of the cooling conduit (e.g., via a control system operatively coupled to one or more valves and pumps for controlling fluid flow, and actuators for controlling cooling conduit position).

Figure 3:
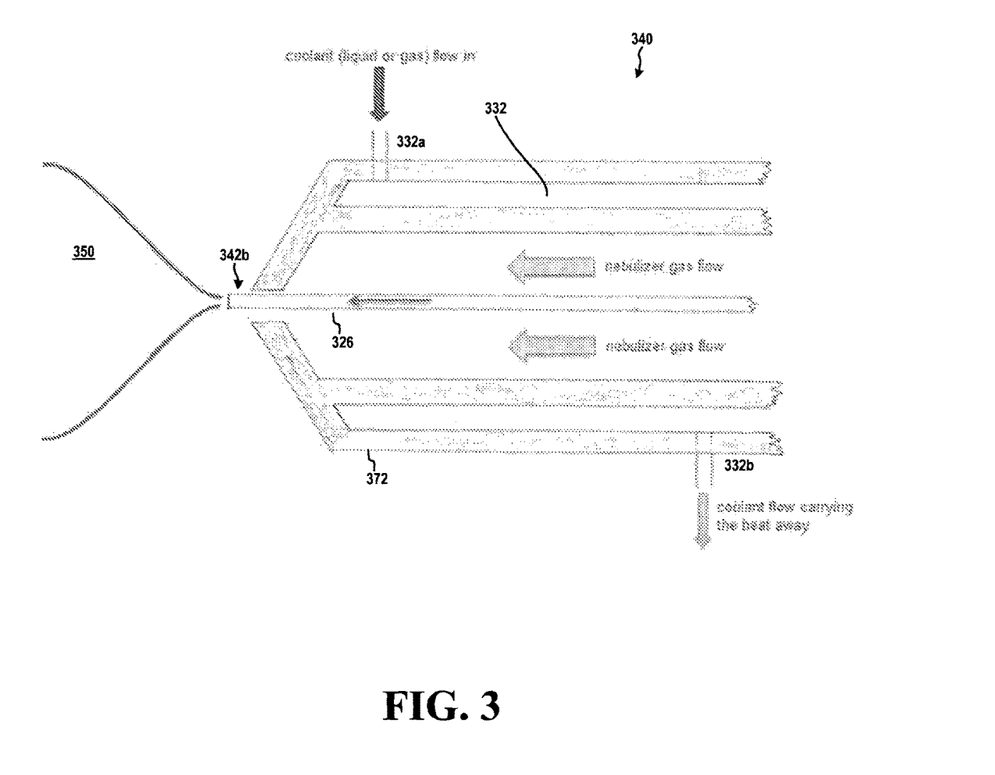
FIG. 3, in schematic diagram, illustrates another exemplary embodiment of an ion probe cooling mechanism according to various aspects of the applicants' teachings.

With reference now to FIG. 3, another exemplary embodiment of a cooling mechanism for maintaining the ion probe 342 at or below a desired temperature is schematically depicted. As in the exemplary embodiments discussed above, the ion source 340 of FIG. 3 includes a sheath (e.g., nebulizer shaft 372), within which the ion probe 342 is at least partially disposed along its length. The nebulizer shaft 372 thus defines a channel between an inner wall of the nebulizer shaft 372 and an outer wall of the ion probe 342, and within which a nebulizing gas flow can be provided to interact with the fluid discharged from the outlet end 342b of the ion probe 342 to generate a sample plume 350. The nebulizer shaft 372 differs from the nebulizer shaft 72 described above with reference to FIGS. 1 and 2, however, in that one or more cooling fluid flow channels 332 are formed within the nebulizer shaft 372. In this manner, cooling fluid can be pumped into the nebulizer shaft 372 (e.g., via inlet port 332a), circulate within the flow channels 332, which shields the ion probe 342 from the external heat and is in thermal contact with the ion probe 342 to extract heat therefrom, and exit the nebulizer shaft 372 (e.g., via outlet port 332b). As will be appreciated, the cooling fluid can be recirculated within a closed system (e.g., the fluid can be re-cooled via a heat exchanger and circulated again within the nebulizer shaft 372), or alternatively can be disposed of after removing heat from the probe 342.

Though the exemplary fluid flow channels 332 depicted in FIG. 3 extend circumferentially around and within the nebulizer shaft 372, it will be appreciated that one or more channels (not shown) can extend from an inner surface of the nebulizer shaft 372 across the channel so as to be in direct contact with the outer surface of the ion probe 342 without blocking nebulizer gas flow within the channel.

Systems and methods that incorporate a cooling mechanism in accordance with the present teachings to maintain the ion probe at a temperature below which deleterious effects on the sample plume are observed can provide a number of advantages over prior art systems. In some embodiments, for example, the transfer of heat away from the ion probe can be effective to maintain the ion probe at a temperature below the vaporization temperature of the liquid sample substantially along its entire length. For example, the cooling mechanism can be configured to maintain the ion probe at a temperature less than about 60° C. throughout its entire length. In this manner, issues related to overheated ion sources (e.g., instability of the ion signal due to vaporization of the liquid sample within the ion probe) can be prevented or corrected without having to take the ion source 40 off line to cool the probe. Moreover, because overheating of the ion source may be particularly troublesome during long sample runs and/or with low flow rate discharge from the ion source (e.g., due to the increased dwell time of the liquid sample within the ion probe), the ability to maintain the temperature of and/or reduce the temperature of an ion probe may beneficially prevent aborted experiments due to thermal interruption of the ion source, enable the use of an increased range of sample sources, and/or enable the use of higher desolvation temperatures. Finally, cooling mechanisms in accordance with various aspects of the present teachings can provide a variety of parameters (e.g., cooling fluid composition, cooling fluid flow rate, cooling conduit positioning) that can be selected to optimize the temperature of the ion probe, which as surprisingly demonstrated in the following examples, may ultimately lead to an overall increase in sensitivity of the mass spectrometer system. Thus, unlike prior art systems in which the heater may require adjustment away from optimal desolvation temperatures to ensure stability of the ion sampling, the systems and methods described herein can cool the ion probe to ensure stability of the ion source while maintaining optimal desolvation and mass spectrometer performance (e.g., sensitivity).

EXAMPLES

The applicants' teachings can be more fully understood with reference to the examples and resulting data that follow. Other embodiments of the applicants' teachings will be apparent to those skilled in the art from consideration of the present specification and practice of the present teachings disclosed herein. It is intended that these examples be considered as exemplary only. The examples are provided for illustrative purposes and do not necessarily indicate optimal ways of implementing applicants' teachings or optimal results that can be obtained.

Figure 4:
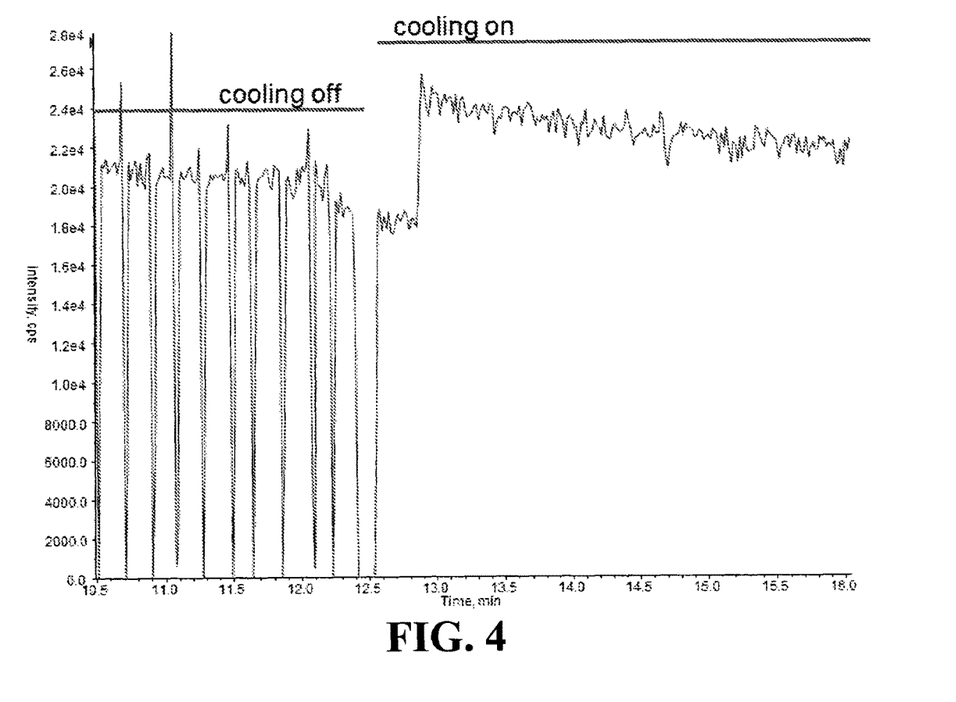
FIG. 4 presents data from one exemplary embodiment of a system and method utilizing the probe cooling mechanism of FIG. 2.

The cooling of the ion source in systems and methods according to the teachings herein can result in improved stability of the ion signal relative to that produced by un-cooled prior art ion sources. For example, a prototype system employing a cooling conduit 32 for discharging a cooling fluid within the channel of the nebulizer shaft 72 as described in FIGS. 1 and 2 was produced to generate the exemplary histogram depicted in FIG. 4. The histogram of FIG. 4 compares the detection signals generated by an API 3200 mass spectrometer modified in accordance with the present teachings and that employed an ion source (e.g., an ESI-assisted nebulizer operating at 10 μL/min of a liquid sample containing 50% water, 50% methanol, and 0.1% formic acid), as the cooling conduit 32 was switched between an inactive state and an active state. Throughout the sample run, standard settings for the nebulizer gas and desolvation heaters (~1.5 L/min and ~8 L/min respectively) were applied. The ionization chamber was substantially maintained at a temperature of about 500° C. While the cooling mechanism was active, cooling fluid comprising 50% methanol and 50% water was discharged from the cooling conduit 32 at a volumetric flow rate of approximately 40 μL/min. As seen in FIG. 4, the ion signal generally becomes unstable as heat within the ion probe builds up. That is, the signal spikes as the sample plume experiences cycles of increased signal and no signal as vapor plugs caused by overheating repeatedly pass through the un-cooled ion probe. However, upon activating the cooling mechanism to deliver a cooling fluid into the channel of the nebulizer, the signal becomes stabilized as seen on the right side of FIG. 4.

Figure 5:
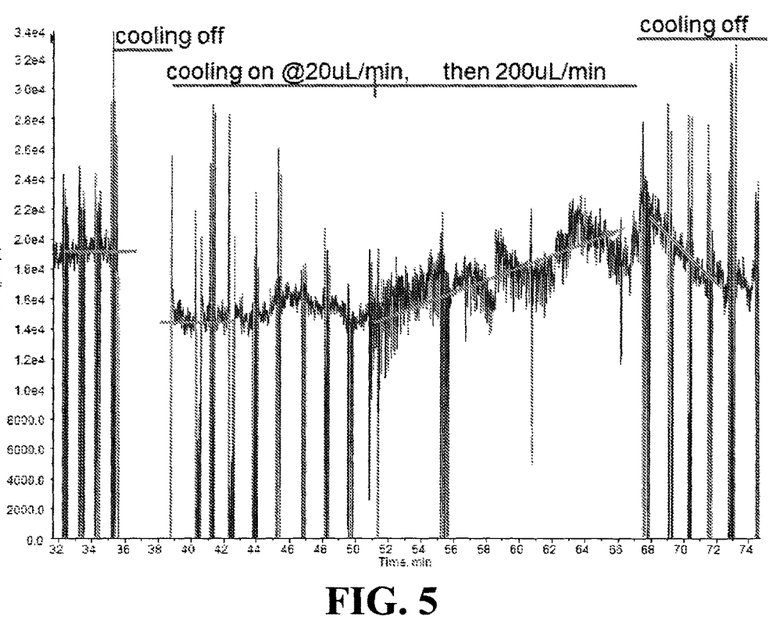
FIG. 5 presents additional data from one exemplary embodiment of a system and method utilizing the probe cooling mechanism of FIG. 2.

Surprisingly, it was discovered that active cooling of the ion source using systems and methods according to the teachings herein may result not only in improved stability of the ion sampling, but also improved sensitivity. With reference now to FIG. 5, which utilized the same prototype system employed to generate the histogram of FIG. 4, it was observed that the system initially generates an unstable ion signal (i.e., without cooling). Cooling of the ion probe is then initiated by delivering through the cooling conduit 32 cooling fluid comprising 100% methanol at a volumetric flow rate of approximately 20 μL/min. Under these experimental conditions, this low flow rate is insufficient to save the source from generating an unstable sample plume. However, when the fluid flow rate of the cooling liquid is increased to approximately 200 μL/min, the ion source stabilizes, as indicated in the reduction of signal spiking.

Moreover, not only does the stability increase under these cooling parameters, but the histogram additionally indicates a signal increase over time (i.e., an overall increase in sensitivity as the ion probe is cooled). Finally, upon deactivating the cooling mechanism, the signal again becomes unstable as heat begins to build up in the ion probe. Based on these data, it is believed that further optimization of the cooling parameters (e.g., through the selection of one or more of cooling fluid composition, cooling fluid flow rate, cooling conduit positioning) and/or active control of the cooling may not only maintain the ion probe at temperatures below which deleterious effects on the ion signal are observed, but may also provide for significant gains in sampling efficiency (e.g., higher desolvation efficiency) and ultimately detection sensitivity.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Those having ordinary skill in the art will appreciate that various changes can be made to the above embodiments without departing from the scope of the invention. All such modifications or variations are believed to be within the sphere and scope of the applicants' teachings as defined by the claims appended hereto.

The invention claimed is:

1. An ion source for generating ions for delivery to a mass spectrometer, comprising:
   a chamber configured to be in fluid communication with a mass spectrometer system via a sampling orifice;
   a sample conduit for discharging a liquid sample into said chamber, said conduit extending from a proximal, inlet end configured to receive a liquid sample from a sample source and terminating in a distal, outlet end extending into said chamber;
   a sheath surrounding said sample conduit so as to define a channel between an inner wall of said sheath and said conduit, said channel configured to provide a nebulizer gas flow at the outlet end of said sample conduit for generating a sample plume comprising a plurality of droplets of said discharged sample and said nebulizer gas directed substantially toward said sampling orifice; and
   a cooling conduit having an outlet for delivering a cooling fluid to the channel, the outlet of the cooling conduit is configured to deliver said cooling fluid to a surface of the sample conduit within said sheath for removing heat therefrom, wherein said cooling liquid is configured to remove heat from said sample conduit via evaporation of the cooling liquid upon contact with said sample conduit.

2. The ion source of claim 1, wherein the outlet of said cooling conduit comprises a nozzle for generating a spray of the cooling fluid within said channel.

3. The ion source of claim 1, wherein said cooling conduit is at least partially disposed within the channel.

4. The ion source of claim 1, wherein said outlet of the cooling conduit is configured to move axially within the channel between a first, proximal position and a second, distal position.

5. The ion source of claim 4, wherein movement of the outlet end of the cooling conduit between the first and second positions is effective to modify a rate of cooling of the sample conduit.

6. The ion source of claim 1, further comprising a pump for controlling a rate of cooling fluid flow through said cooling conduit.

7. The ion source of claim 1, further comprising a cooling fluid source fluidly coupled to the cooling conduit.

8. The ion source of claim 1, wherein the cooling fluid is selected such that substantially all of the cooling fluid discharged into the channel is configured to change its phase following contact with the conduit.

9. The ion source of claim 1, wherein at least one of a fluid flow rate of cooling fluid, a position of the outlet of the cooling conduit, and a composition of the cooling fluid are selected so as to control a temperature of the sample conduit.

10. The ion source of claim 9, wherein one or more of the fluid flow rate of cooling fluid, the position of the outlet of the cooling conduit, and the composition of the cooling fluid are selected so as to maintain the sample conduit at a temperature below about 60° C. substantially along its entire length.

11. The ion source of claim 1, wherein the liquid sample has a fluid flow rate through said sample conduit in a range of between about 1 µL/min to about 10 mL/min.

12. A method for directing ions to a mass spectrometer, the method comprising:
    receiving a liquid sample from a sample source at an inlet end of a sample conduit extending through a channel defined by a sheath surrounding said sample conduit;
    providing a nebulizer gas flow within said channel;
    discharging the liquid sample and the nebulizer gas flow into a chamber in fluid communication with a mass spectrometer via a sampling orifice, the liquid sample and the nebulizer gas flow forming a plume comprising a plurality of liquid sample droplets;
    heating the chamber so as to promote desolvation of the plurality of droplets within said plume;
    delivering a cooling fluid into said channel for removing heat therefrom, wherein said cooling liquid is configured to remove heat from said sample conduit via evaporation of the cooling liquid upon contact with said sample conduit.

13. The method of claim 12, wherein delivering the cooling fluid into said channel comprises delivering said cooling fluid to a surface of the sample conduit within said sheath.

14. The method of claim 12, wherein said cooling fluid removes heat from said sample conduit via evaporation of the cooling liquid upon contact with said sample conduit.

15. The method of claim 12, further comprising adjusting a rate of cooling of the sample conduit.

16. The method of claim 15, wherein adjusting the rate of cooling comprises adjusting one or more of a flow rate of cooling fluid, a position of an outlet of a cooling conduit, and a composition of the cooling fluid so as to control a temperature of the sample conduit.

17. The method of claim 16, wherein one or more of the flow rate of cooling fluid, the position of the outlet of the cooling conduit, and the composition of the cooling fluid are adjusted such that substantially all of the cooling fluid discharged into the channel changes phase prior to discharge from the channel into the chamber.

18. The method of claim 12, wherein the cooling fluid comprises at least one of water and methanol.

\* \* \* \* \*